US011254724B2

(12) United States Patent
Jung et al.

(10) Patent No.: US 11,254,724 B2
(45) Date of Patent: Feb. 22, 2022

(54) GLUCAGON DERIVATIVES

(71) Applicant: HANMI PHARM CO., LTD., Gyeonggi-do (KR)

(72) Inventors: Sung Youb Jung, Gyeonggi-do (KR); Young Jin Park, Gyeonggi-do (KR); Jong Suk Lee, Gyeonggi-do (KR); Jae Hyuk Choi, Gyeonggi-do (KR); Chang Ki Lim, Gyeonggi-do (KR); Se Chang Kwon, Gyeonggi-do (KR)

(73) Assignee: Hanmi Pharm. Co., Ltd., Hwaseong-Si (KR)

( * ) Notice: Subject to any disclaimer, the term of this patent is extended or adjusted under 35 U.S.C. 154(b) by 0 days.

(21) Appl. No.: 16/684,110

(22) Filed: Nov. 14, 2019

(65) Prior Publication Data
US 2020/0140515 A1 May 7, 2020

Related U.S. Application Data

(62) Division of application No. 15/539,238, filed as application No. PCT/KR2015/014481 on Dec. 30, 2015, now Pat. No. 10,513,550.

(30) Foreign Application Priority Data

Dec. 30, 2014 (KR) ........................ 10-2014-0193691

(51) Int. Cl.
*C07K 14/605* (2006.01)
*A61K 38/26* (2006.01)
*A61K 45/06* (2006.01)
*A61K 38/00* (2006.01)

(52) U.S. Cl.
CPC ............ *C07K 14/605* (2013.01); *A61K 38/26* (2013.01); *A61K 45/06* (2013.01); *A61K 38/00* (2013.01)

(58) Field of Classification Search
CPC .............................. C07K 14/605; A61K 38/26
See application file for complete search history.

(56) References Cited

U.S. PATENT DOCUMENTS

| 6,776,983 | B1 | 8/2004 | Shuji et al. |
| 7,217,845 | B2 | 5/2007 | Rosen et al. |
| 7,521,424 | B2 | 4/2009 | Rosen et al. |
| 7,737,260 | B2 | 6/2010 | Kim et al. |
| 7,928,058 | B2 | 4/2011 | Sinha et al. |
| 8,263,084 | B2 | 9/2012 | Song et al. |
| 8,729,017 | B2 | 5/2014 | DiMarchi et al. |
| 8,778,872 | B2 | 7/2014 | DiMarchi et al. |
| 8,975,001 | B2 | 3/2015 | Bae |
| 9,522,946 | B2 | 12/2016 | Jung et al. |
| 9,527,898 | B2 | 12/2016 | Jung et al. |
| 9,724,420 | B2 | 8/2017 | Kim et al. |
| 9,731,031 | B2 | 8/2017 | Jung et al. |
| 9,765,131 | B2 | 9/2017 | Jung et al. |
| 10,279,041 | B2 | 5/2019 | Kim et al. |
| 10,493,132 | B2 | 12/2019 | Jung et al. |
| 2003/0032588 | A1 | 2/2003 | Marshall et al. |
| 2004/0087778 | A1 | 5/2004 | Feige et al. |
| 2006/0269553 | A1 | 11/2006 | Kim et al. |
| 2009/0053246 | A1 | 2/2009 | Kim et al. |
| 2009/0181037 | A1 | 7/2009 | Heavner |
| 2009/0238838 | A1 | 9/2009 | Kim et al. |
| 2009/0297496 | A1 | 12/2009 | Grabowski |
| 2009/0298757 | A1 | 12/2009 | Bloom et al. |
| 2010/0144617 | A1 | 6/2010 | Sinha Roy et al. |
| 2010/0190701 | A1 | 7/2010 | Day et al. |
| 2010/0196405 | A1 | 8/2010 | Ng |
| 2010/0239554 | A1 | 9/2010 | Schellenberger et al. |
| 2010/0330108 | A1 | 12/2010 | Song et al. |
| 2011/0034374 | A1 | 2/2011 | Bloom et al. |
| 2011/0065633 | A1 | 3/2011 | DiMarchi et al. |
| 2011/0152182 | A1 | 6/2011 | Alsina-Fernandez et al. |
| 2011/0190200 | A1 | 8/2011 | DiMarchi et al. |
| 2012/0003712 | A1 | 1/2012 | Song et al. |
| 2012/0165503 | A1 | 6/2012 | Carrington et al. |
| 2012/0178670 | A1 | 7/2012 | Riber et al. |
| 2012/0329707 | A1 | 12/2012 | DiMarchi et al. |
| 2013/0035285 | A1 | 2/2013 | Lau et al. |
| 2013/0122023 | A1 | 5/2013 | Woo et al. |
| 2014/0128318 | A1 | 5/2014 | Jung et al. |

FOREIGN PATENT DOCUMENTS

| CN | 101213209 A | 7/2008 |
| CN | 101389648 A | 3/2009 |
| CN | 101578107 A | 11/2009 |
| CN | 101974077 A | 2/2011 |
| CN | 102010473 A | 4/2011 |
| CN | 102369209 A | 3/2012 |
| CN | 103732616 A | 4/2014 |
| CN | 103732618 A | 4/2014 |
| EP | 2300037 A2 | 3/2011 |
| EP | 2330124 A2 | 6/2011 |
| EP | 1891105 B1 | 4/2012 |
| EP | 2884994 A1 | 6/2015 |
| JP | 2003-531632 A | 10/2003 |
| JP | 2008-169195 A | 7/2008 |
| JP | 2008-543816 A | 12/2008 |
| JP | 2009-527558 A | 7/2009 |
| JP | 2009-203235 A | 9/2009 |
| JP | 2011-505355 A | 2/2011 |
| JP | 2011-511753 A | 4/2011 |
| JP | 2013-537525 A | 10/2013 |
| JP | 2014-516566 A | 7/2014 |

(Continued)

OTHER PUBLICATIONS

US 8,729,011 B2, 05/2014, DiMarchi (withdrawn)

(Continued)

*Primary Examiner* — Gyan Chandra
(74) *Attorney, Agent, or Firm* — BakerHostetler

(57) ABSTRACT

The present invention relates to a novel peptide of a glucagon derivative and a composition for preventing or treating obesity comprising the peptide as an active ingredient. The glucagon derivative according to the present invention shows a more excellent activating effect with regard to both glucagon-like peptide-1 receptors and glucagon receptors compared to native glucagon, and thus can be widely used as an effective agent for treating obesity.

10 Claims, No Drawings

Specification includes a Sequence Listing.

(56) References Cited

FOREIGN PATENT DOCUMENTS

| | | |
|---|---|---|
| KR | 10-0389726 B1 | 6/2003 |
| KR | 10-2005-0026685 A | 3/2005 |
| KR | 10-0567902 B1 | 4/2006 |
| KR | 10-2006-0106486 A | 10/2006 |
| KR | 10-0725315 B1 | 6/2007 |
| KR | 10-2008-0039375 A | 5/2008 |
| KR | 10-0880509 B1 | 1/2009 |
| KR | 10-2009-0056796 A | 6/2009 |
| KR | 10-2009-0096498 A | 9/2009 |
| KR | 10-2009-0098843 A | 9/2009 |
| KR | 10-0925017 B1 | 11/2009 |
| KR | 10-2010-0043208 A | 4/2010 |
| KR | 10-2010-0105494 A | 9/2010 |
| KR | 10-2011-0039230 A | 4/2011 |
| KR | 10-2011-0056472 A | 5/2011 |
| KR | 10-2012-0043208 A | 5/2012 |
| KR | 10-2012-0052973 A | 5/2012 |
| KR | 10-2012-0064110 A | 6/2012 |
| KR | 10-2012-0137271 A | 12/2012 |
| KR | 10-2012-0139579 A | 12/2012 |
| KR | 10-2014-0018462 A | 2/2014 |
| NZ | 618811 A | 5/2016 |
| NZ | 718999 A | 7/2017 |
| TW | 200848423 A | 12/2008 |
| TW | 201245246 | 11/2012 |
| TW | 201307380 A | 2/2013 |
| TW | 201546053 | 12/2015 |
| WO | 96/32478 A1 | 10/1996 |
| WO | 97/34631 A1 | 9/1997 |
| WO | 2003/022304 A1 | 3/2003 |
| WO | 2004/062685 A2 | 7/2004 |
| WO | 2005/035761 A1 | 4/2005 |
| WO | 2005/087797 A1 | 9/2005 |
| WO | 2006/059106 A2 | 6/2006 |
| WO | 2006/086769 A2 | 8/2006 |
| WO | 2006/107124 A1 | 10/2006 |
| WO | 2006/134340 A2 | 12/2006 |
| WO | 2007/022123 A2 | 2/2007 |
| WO | 2007/100535 A2 | 9/2007 |
| WO | 2007/146038 A2 | 12/2007 |
| WO | 2008/071972 A1 | 6/2008 |
| WO | 2008/082274 A1 | 7/2008 |
| WO | 2008/101017 A2 | 8/2008 |
| WO | 2009/033756 A2 | 3/2009 |
| WO | 2009/058734 A1 | 5/2009 |
| WO | 2009/069983 A2 | 6/2009 |
| WO | 2009/099763 A1 | 8/2009 |
| WO | 2009/155257 A1 | 12/2009 |
| WO | 2009/155258 A2 | 12/2009 |
| WO | 2013/192129 A1 | 12/2009 |
| WO | 2010/013012 A2 | 2/2010 |
| WO | 2010/033207 A1 | 3/2010 |
| WO | 2010/033220 A2 | 3/2010 |
| WO | 2010/070253 A1 | 6/2010 |
| WO | 2010/071807 A1 | 6/2010 |
| WO | 2010/096052 A1 | 8/2010 |
| WO | 2010/096142 A1 | 8/2010 |
| WO | 2010/107256 A2 | 9/2010 |
| WO | 2010/108153 A2 | 9/2010 |
| WO | 2010/148089 A1 | 12/2010 |
| WO | 2011/006497 A1 | 1/2011 |
| WO | 2011/056713 A2 | 5/2011 |
| WO | 2011/071957 A1 | 6/2011 |
| WO | 2011/075393 A2 | 6/2011 |
| WO | 2011/087671 A1 | 7/2011 |
| WO | 2011/087672 A1 | 7/2011 |
| WO | 2011/094337 A1 | 8/2011 |
| WO | 2011/122921 A2 | 10/2011 |
| WO | 2011/143208 A1 | 11/2011 |
| WO | 2011/163012 A2 | 12/2011 |
| WO | 2012/008779 A2 | 1/2012 |
| WO | 2012/011752 A2 | 1/2012 |
| WO | 2012/057525 A2 | 5/2012 |
| WO | 2012/088379 A2 | 6/2012 |
| WO | 2012/169798 A2 | 12/2012 |
| WO | 2012/173422 A1 | 12/2012 |
| WO | 2013/133667 A1 | 9/2013 |
| WO | 2013/157002 A1 | 10/2013 |
| WO | 2014/017843 A1 | 1/2014 |
| WO | 2014/017853 A2 | 1/2014 |
| WO | 2014/049610 A2 | 4/2014 |
| WO | 2014/073842 A1 | 5/2014 |
| WO | 2014/073845 A1 | 5/2014 |

OTHER PUBLICATIONS

Hinke Simon Amadeus et al, "Dipeptidyl peptidase IV (DPIV/CD26) degradation of glucagon: Characterization of glucagon degradation products and DPIV-resistant analogs", Journal of Biological Chemistry, (20000211), vol. 275, No. 6, pp. 3827-3834.

Sakamuri Sukumar et al, "Novel long-acting GLP-1 analogs with superior in vivo bioavailability", Diabetes, & 67TH Annual Meeting of the American—Diabetes—Association; Chicago, IL, USA; Jun. 22-26, 2007, (200706), vol. 56, No. Suppl. 1, p. A151.

"Obesity", Merck Manual, http://www.merckmanuals.com/professoinal/nutritional_disorders/obesity_and_the_metab., accessed Oct. 6, 2014, 1-9.

"Prescription Medications for the Treatment of Obesity", U.S. Department of Health and Human Services, Apr. 1-8, 2013.

Berendsen, "A Glimpse of the Holy Grail?", Science, 1998, 282, 642-643.

Berger et al., "The Effect of Treatment of Type 2 (Insulin Independent) Diabetes Meilitus on Plasma Concentrations of Pancreatic Polypeptide and Glucagon", Diabetologia, 1981, 21, 120-125.

Bradley et al., Limits of Cooperativity in a Structurally Modular Protein: Response of the Notch Ankyrin Domain to Analogous Alanine Substitutions in Each Repeat, J. Mol. BloL (2002) 324, 373-386.

Campbell et al., "Pharmacology, Physiology, and Mechanisms of Incretin Hormone Action", Cell Metabolism, Jun. 4, 2013, 17, 819-837.

Chao-Lin et al., "Review on the effect of glucagon-like peptide-1 receptor agonists and dipeptidyl peptidase-4 inhibitors for the treatment of non-alcoholic fatty liver disease", Huashong University of Science and Technology Journal, vol. 35, No. 3, Jun. 1, 2015, pp. 333-336.

Chao-lin Li et al., "Review on the effect of glucagon-like peptide-1 receptor agonists and dipeptidyl peptidase-4 inhibitors for the treatment of non-alcoholic fatty liver disease", Huashong University of Science and Technology Journal, vol. 35, No. 3, Jun. 1, 2015, pp. 333-336.

Clark et al., "Identifying and Managing Patients with Hyperlipidemia", The American Journal of Managed Care, Aug. 1997, vol. 3, No. 8, 1211-1219.

Collie et al., Purification and sequence of rat oxyntomodulin, Proc. Natl. Acad. Sci. USA, 1994, 91, pp. 9362-9366.

Day et al., A new glucagon and GLP-1 co-agonist eliminates obesity in rodents, Nature Chemical Biology, 2009, 5, pp. 749-757.

Day et al., Optimization of Co-Agonism at GLP-1 and Glucagon Receptors to Safely Maximize Weight Reduction in DIO—Rodents, Peptide Science, 2012, 98, pp. 443-450, published online Apr. 14, 2012.

Definition of prophylactic, from http://www.merriam-webster.com/dictionary/prophylactic, pp. 1-3, accessed Feb. 8, 2015.

Dhanesha et al., "Treatment with exendin-4 improves the antidiabetic efficacy and reverses hepatic steatosis in glucokinase activator treated db/db mice", European Journal of Pharmacology, vol. 714, No. 1, Jun. 25, 2013, pp. 188-192.

Diabetes, from http://www.merckmanuals.com/professional/endocrine-and-metabolic-disorders/..., pp. 1-34, accessed Sep. 2, 2016.

Ding et al., Exendin-4, a Glucagon-Like Protein-1 (GLP-1) Receptor Agonist, Reverses Hepatic Steatosis in ob/ob Mice, Hepatology, 2006, 43, pp. 173-181.

Drucker, "Glucagon-Like Peptides", Diabetes, Feb. 1998, vol. 47, 159-169.

(56) References Cited

OTHER PUBLICATIONS

Eaton, Hypolipemic action of glucagon in experimental endogenous lipemia in the rat, Journal of Lipid Research, 1973, 14, pp. 312-318.
Eguchi et al., "Pilot study of liraglutide effects in non-alcoholic steatohepatitis and non-alcoholic fatty liver disease with glucose intolerance in Japanese patients (LEAN-J)", Hepatology Research, 2015, 45, 269-278.
English Translation of Chinese Patent Application No. 201280038851. 4: Notification of Second Office Action dated Sep. 15, 2015, 9 pages.
English translation of Japanese Patent Application No. 2014-515759: Notice of Reason for Rejection dated Dec. 15, 2015, 5 pages.
European Patent Office, "Supplementary European Search Report", dated Dec. 3, 2014, issued in counterpart Application No. 12797363.4, 5 pages.
European Patent Office, "Supplementary European Search Report", dated Oct. 13, 2014, issued in counterpart Application No. 12801247.3, 7 pages.
European Patent Office, "Supplementary Partial European Search Report", dated Feb. 25, 2016, issued in counterpart Application No. 13823727.6, 7 pages.
Frankel et al., "Characterization of diphtheria fusion proteins targeted to the human interleukin-3 receptor", Protein Engineering, 2000, vol. 13, No. 8, pp. 575-581.
Franz et al., "The Dilemma of Weight Loss in Diabetes", Diabetes Spectrum, 2007, vol. 20, No. 3, 133-136.
Goldberg, "Dyslipidemia", Dyslipidemia—Endocrine and Metabolic Disorders—Merck Manuals Professional Edition, http://www.merckmanuals.com/professional/endocrine-and-metabolic-diorders-/lipid-dis . , accessed Dec. 29, 2015, 11 pages.
Habegger et al., The metabolic actions of glucagon revisited, Nat. Rev. Endocrinol., 2010, 6, pp. 689-697.
Hepatitis Health Center, "Fatty Liver Disease", http://www.webmd.com/hepatitis/fatty-liver-diseasepage=2&print=true, accessed Dec. 29, 2015, pp. 1-4.
International Patent Application No. PCT/KR2012/004722: International Search Report and Written Opinion dated Nov. 14, 2012, 6 pages.
International Patent Application No. PCT/KR2013/006668: International Search Report and Written Opinion dated Oct. 21, 2013, 10 pages.
International Patent Application No. PCT/KR2013/009986: International Search Report and Written Opinion dated Jan. 29, 2014, 11 pages.
International Patent Application No. PCT/KR2013/009990: International Search Report and Written Opinion dated Jan. 20, 2014, 12 pages.
Japan Patent Office, "Grounds for Rejection", dated Dec. 15, 2015, issued in corresponding Japanese Application 2014/515759, 12 pages.
Japan Patent Office, "Grounds for Rejection", dated Nov. 24, 2015, issued in corresponding Japanese Application No. 2014-514799, 9 pages.
K Wynne et al., "Oxyntomodulin increases energy expenditure in addition to decreasing energy intake in overweight and obese humans: a randomised controlled trial", International Journal of Obesity (2006) 30, pp. 1729-1736.
Kerr et al., "(-Ser)Oxm[mPEG-PAL]: a novel chemically modified analogue of oxyntomodulin with antihyperglycaemic, insulinotropic and anorexigenic actions", Biochemical Pharmacology, 2010, 80(11), 1727-1735.
Kerr et al., "(D-Ser2)Oxm[mPEG-PAL]: A novel modified analogue of oxyntomodulin with antihyperglycaemic, insullinotropic and anorexigenic actions", Biochemical Pharmacology, Dec. 2010, vol. 80, Issue 11, 1727-1735.
Korean Intellectual Property Office, "Notice of Preliminary Rejection", dated Nov. 20, 2014, issued in corresponding Korean Application No. 10-2012-0061166, 7 pages.
Lam, "Atherosclerosis", Atherosclerosis—Cardiovascular Disorders—Merck Manuals Professional Edition, http://www.merkmanuals.com/professional/cardiovascular-disorder/arteriosc-lerosis/atherosclerosis, accessed Dec. 29, 2015, 1-14.
Lam, "Definition of Arteriosclerosis", http://www.merkmanuals.com/professional/cardiovascular-disorders/arterios-clerosis/defi . , accessed Dec. 29, 2015, 1 page.
Lam, "Nonatheromatous Arteriosclerosis", http://222.merckmanuals.com/profession/cardiovasculardisorders/arterioscl-erosis/non., accessed Dec. 29, 2015, 2 pages.
Merriam Webster, Dictionary: prophylactic, (3 pages total), accessed from the WWW on Feb. 8, 2015. (3pgs.) URL http://www.merriam-webster.com/dictionary/prophylactic.
Nakazato, Obesity: Progress in Diagnosis and Treatment; Topics, II. Progress in Treatment; 2. Drug strategies for the treatment of obesity—clinical application of gut-brain peptides, Japan Internal Medicine Journal, Apr. 10, 2011, vol. 100, pp. 928-933.
Neuschwander-Tetri et al., "Improved Nonalcoholic Steatohepatitis After 48 Weeks of Treatment With the PPAR-y Ligand Rosiglitazone", Hepatology, 2003, 38, 1008-1017.
New Zealand Intellectual Property Office, "First Examination Report", dated Oct. 7, 2014, issued in corresponding application No. 618810, 3 pages.
New Zealand Intellectual Property Office, "Further Examination Report", dated Oct. 30, 2015, issued in corresponding application No. 618810, 4 pages.
New Zealand Patent Application No. 718999: Further Examination Report dated Oct. 26, 2016, 3 pages.
Ngo et al., Computational Complexity, Protein Structure Protection, and the Levinthal Paradox, 1994, pp. 491-494.
Obesity Causes, from http://www.hsph.harvard.edu/obesity-prevention-source/obesity-causes/, pp. 1-3, accessed Oct. 6, 2014.
Anonymous: "NCT03486392: A Study to Evaluate the Safety and Efficacy of JNJ-645651 11 in Non-diabetic Severely Obese Participants", • Mar. 30, 2018 (Mar. 30, 2018), pp. 1-9, XP055612060, Retrieved from the Internet URL:https://clinicaltrials.gov/ct2/history/NCT034863927V I=View#StudyPageTop [retrieved on Aug. 9, 2019] p. 1.
Duncan et al., "Influence of surfactants upon protein/peptide adsorption to glass and polypropylene", Int. J. Pharm., 1995, 120, 179-188.
Geigert, "Overview of the Stability and Handling of Recombinant Protein Drugs", J. Parenteral Sci. Tech., 1989, 43, No. 5, 220-224.
Kang et al.: 11 791: The ultra-long acting LAPSGLP/GCGdual agonist,HM12525A, demonstrated safety and prolonged pharmacokinetics in healthy volunteers: a phase 1 first-in-human study 11 , Abstracts Of 51 ST EASD Annual Meeting, vol. 58, Sep. 1, 2015 (Sep. 1, 2015), pp. S380-S381, XP055611972, p. S381.
Norde, "Adsorption of Proteins From Solution at the Solid-Liquid Interface", Adv. Colloid Interface Sci., 1986, 25, 267-340.
Tarelli et al., "Recombinant Human Albumin as a Stabilizer for Biological Materials and for the Preparation of International Reference Reagents", Biologicals, 1998, 26, 331-346.
Wang, "Instability, stabilization, and formulation of liquid protein pharmaceuticals", Int. J. Pharm., 1999, 185, 129-188.
Wong, "Pharmaceutical Excipients for the Stabilization of Proteins", Pharm. Tech. Oct. 1997, 34-48.
Olaywi et al., "Novel anti-diabetic agents in non-alcoholic fatty liver disease: a mini-review", Hepatobiliary Pancreat Dis Int, Dec. 15, 2013, vol. 12, No. 6, 584-588.
Olokoba et al., "Type 2 Diabetes Mellitus: A Review of Current Trends", Oman Medical Journal, 2012, vol. 27, No. 4, 269-273.
Park et al., "Dietary and Genetic Obesity Promote Liver Inflammation and Tumorigenesis by Enhancing IL-6 and TNF Expression", Cell, Jan. 22, 2010, 140, 197-208.
Pocai et al., "Glucagon-like peptide 1/glucagon receptor dual agonism reverses obesity in mice", Diabetes, 2009, vol. 58, No. 10, 2253-2266.
Rudinger, "Characteristics of the amino acids as components of a peptide hormone sequence", Peptide Hormones, JA Parsons Ed., 1976, pp. 1-7.
Santoprete et al., "DPP-IV-resistant, long acting oxyntomodulin derivatives", Journal of Peptide Science, Feb. 2011, vol. 17, No. 4, 270-280.

(56) References Cited

OTHER PUBLICATIONS

Seok et al., "Exendin-4 Improves Nonalcoholic Fatty Liver Disease by Regulating Glucose Transporter 4 Expression in ob/ob Mice", Korean Journal of Physiology and Pharmacology, Jan. 1, 2014, p. 333.
Shani Ben-Shlomo et al., "Glucagon-like pepetide-1 reduces hepatic lipogenesis via activation of AMP-activated protein kinase", Journal of Hepatology, Sep. 27, 2010, vol. 54, No. 6, pp. 1214-1223.
Shigeru, "Obesity and Metabolic Syndrome", Tokyo Internal Medical Association Seminar 2008 Special Lecture, Dec. 2008, vol. 24, No. 2, 8 pages.
Sigma-Aldrich, "Exendin-4 sequence", http://www.simgaaldrich.com/catalog/product/sigma/e7144lang=en®ion=US, accessed Dec. 28, 2015, 1 page.
Skosyrev et al., "The Dependence of Stability of the Green Fluorescent Protein-Obelin Hybrids on the Nature of Their Constituent Modules and the Structure of the Amino Acid Linker", Russian Journal of Bioorganic Chemistry, 2001, vol. 27, No. 5, pp. 323-329.
State Intellectual Property Office of PRC, "Notification of First Office Action", dated Jan. 7, 2015 issued in corresponding Chinese Application No. 201280039781.4, 21 pages.
State Intellectual Property Office of PRC, "Notification of Second Office Action", dated Sep. 15, 2015, issued in corresponding Chinese Application No. 201280038851.4, 15 pages.
State Intellectual Property Office of PRC, English translation of communication dated Mar. 6, 2015, issued in corresponding Chinese Application No. 201280038851.4 (submitted without translation on Jun. 24, 2015).
Taiwanese Intellectual Property Office, "Examination Report", dated Dec. 23, 2013 issued in corresponding application No. 101121483, 15 pages.
Taiwanese Patent Office, Communication dated Mar. 11, 2014 issued in corresponding Tawinese Patent Application No. 101120633.
Treethammathurot et al., "Effect of PEG molecular weight and linking chemistry on the biological activity and thermal stability of PEGylated trypsin", International Journal of Pharmaceutics, 2008, vol. 357, pp. 252-259.
U.S. Appl. No. 14/124,969: Communication dated Jun. 25, 2014, 12 pages.
U.S. Appl. No. 14/124,969: Final Rejection dated Apr. 14, 2015, 17 pages.
U.S. Appl. No. 14/124,969: Non-Final Rejection dated Dec. 10, 2014, 40 pages.
U.S. Appl. No. 14/126,914: Communication, dated Sep. 18, 2014, 14 pages.
U.S. Appl. No. 14/126,914: Examiner Initialed Interview, dated Feb. 29, 2016, 1 page.
U.S. Appl. No. 14/126,914: Non-Final Rejection, dated Mar. 5, 2015, 35 pages.
U.S. Appl. No. 14/415,200: Non-Final Rejection dated Jan. 20, 2016, 39 pages.
U.S. Appl. No. 14/748,389: Non-Final Rejection, dated Jan. 13, 2016, 18 pages.
Vitamins & Supplements Search, http://www.webmd.com/vitamins-supplements/condition-1275-Hyperlipidemia.a- spx, accessed Dec. 29, 2015, pp. 1-3.
Voet et al., "Abnormal Hemoglobins", Biochemistry, John Wiley & Sons Inc., 1995, 235-241.
Water, from http://www.biology-online.org/dictionary/Water, pp. 1-3, accessed Apr. 24, 2014.
Watts et al., "Prediction of Glucose Response to Weight Loss in Patients With Non-Insulin-Dependent Diabetes Mellitus", Arch Intern Med, Apr. 1990, vol. 150, 803-806.
What Causes Overweight and Obesity?, from http://www.nhlbi.nih.gov/health/health-topics/topics/obe/causes.html, pp. 1-5, accessed Oct. 6, 2014.
World Health Organization, Global Strategy on Diet, Physical Activity and Health, 2004.
Wynne et al., "Subcutaneous Oxyntomodulin Reduces Body Weight in Overweight and Obese Subjects A Double-Blind, Randomized, Controlled Trial", Diabetes, Aug. 2005, vol. 54, pp. 2390-2395.
Wynne et al., "Oxyntomodulin increases energy expediture in addition to decreasing energy intake in overweight and obese humans: a randomised controlled trial," International Journal of Obesity, 2006, 30, 1729-1736.
Xu et al., "SIRT1 mediates the effect of GLP-1 receptor agonist exenatide on ameliorating hepatic steatosis", Diabetes, Jun. 19, 2014, vol. 63, No. 11, 3637-3646.
Zhou et al., "Role of AMP-activated protein kinase in mechanism of metformin action", J. Clinical Invest., 2001, 108, 1167-1174.

SEQUENCE LISTING

```
<160> NUMBER OF SEQ ID NOS: 19

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 2

His Xaa Gln Gly Thr Phe Thr Ser Asp Tyr Ser Lys Tyr Leu Asp Glu
1               5                   10                  15

Lys Cys Ala Lys Glu Phe Ile Gln Trp Leu Val Asn Thr
            20                  25

<210> SEQ ID NO 3
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 3

His Xaa Gln Gly Thr Phe Thr Ser Asp Tyr Ser Lys Tyr Leu Asp Glu
1               5                   10                  15

Lys Cys Val Lys Leu Phe Ile Gln Trp Leu Val Asn Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 4

His Xaa Gln Gly Thr Phe Thr Ser Asp Tyr Ser Lys Tyr Leu Asp Glu
1               5                   10                  15

Lys Cys Ala Lys Glu Phe Val Glu Trp Leu Val Asn Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 5

His Xaa Gln Gly Thr Phe Thr Ser Asp Tyr Ser Lys Tyr Leu Asp Glu
1               5                   10                  15

Lys Cys Ala His Glu Phe Val Glu Trp Leu Val Asn Thr
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 6

His Xaa Gln Gly Thr Phe Thr Ser Asp Tyr Ser Lys Tyr Leu Asp Ser
1               5                   10                  15

Lys Cys Ala His Glu Phe Val Glu Trp Leu Val Asn Thr
            20                  25
```

```
<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 7

His Xaa Gln Gly Thr Phe Thr Ser Asp Tyr Ser Lys Tyr Leu Asp Ser
1               5                   10                  15

Lys Cys Val His Glu Phe Ile Glu Trp Leu Lys Asn Thr
            20                  25

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 8

His Xaa Gln Gly Thr Phe Thr Ser Asp Tyr Ser Lys Tyr Leu Asp Ser
1               5                   10                  15

Lys Cys Ala His Glu Phe Ile Glu Trp Leu Lys Asn Lys
            20                  25

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 9

His Xaa Gln Gly Thr Phe Thr Ser Asp Tyr Ser Lys Tyr Leu Asp Ser
1               5                   10                  15

Glu Cys Ala His Glu Phe Ile Glu Trp Leu Lys Gln Gly
            20                  25

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu
```

```
<400> SEQUENCE: 10

His Xaa Gln Gly Thr Phe Thr Ser Asp Tyr Ser Lys Tyr Leu Asp Asp
1               5                   10                  15

Lys Cys Ala His Glu Phe Val Glu Trp Leu Val Asn Thr
            20                  25

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 11

His Xaa Gln Gly Thr Phe Thr Ser Asp Tyr Ser Lys Tyr Leu Asp Glu
1               5                   10                  15

Glu Cys Ala Lys Glu Phe Ile Arg Trp Leu Lys Lys Gly
            20                  25

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 12

His Xaa Gln Gly Thr Phe Thr Ser Asp Tyr Ser Lys Tyr Leu Cys Glu
1               5                   10                  15

Lys Arg Ala Lys Glu Phe Val Gln Trp Leu Met Asn Thr
            20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Alpha-methyl-Glu

<400> SEQUENCE: 13

His Xaa Gln Gly Thr Phe Thr Ser Asp Tyr Ser Lys Tyr Leu Asp Glu
1               5                   10                  15

Cys Arg Ala Lys Glu Phe Val Gln Trp Leu Met Asn Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<221> NAME/KEY: MOD_RES
<222> LOCATION: (2)..(2)
<223> OTHER INFORMATION: Alpha-methyl-Glu

<400> SEQUENCE: 14

His Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cccggccccc gcggccgcta ttcgaaatac                                    30

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaacggtccg gaggacgtcg actcttaaga tag                                33

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagcgacacc gaccgtcccc ccgtacttaa ggcc                               34

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctaaccgact ctcggggaag actgagctcg cc                                 32

<210> SEQ ID NO 19
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His, desamino-histidyl, N-dimethyl-histidyl,
      Beta-hydroxy imidazopropionyl, 4-imidazoacetyl, Beta-carboxy
      imidazopropionyl or Tyr

```
<220> FEATURE:
<221> NAME/KEY: MOD_RES
<222> LOCATION: (2)..(2)
<223> OTHER INFORMATION: Alpha-methyl-Glu, aminoisobutyric acid (Aib),
      D-Ala, Gly, Sar(N-methylglycine), Ser or D-Ser
<220> FEATURE:
<221> NAME/KEY: MOD_RES
<222> LOCATION: (15)..(15)
<223> OTHER INFORMATION: Cys, Asp or Glu
<220> FEATURE:
<221> NAME/KEY: MOD_RES
<222> LOCATION: (16)..(16)
<223> OTHER INFORMATION: Glu, Asp, Ser, alpha-methyl-Glu or absent
<220> FEATURE:
<221> NAME/KEY: MOD_RES
<222> LOCATION: (17)..(17)
<223> OTHER INFORMATION: Cys, Gln, Glu, Lys, Arg, Ser or absent
<220> FEATURE:
<221> NAME/KEY: MOD_RES
<222> LOCATION: (18)..(18)
<223> OTHER INFORMATION: Cys, Ala, Arg, Val or absent
<220> FEATURE:
<221> NAME/KEY: MOD_RES
<222> LOCATION: (19)..(19)
<223> OTHER INFORMATION: Ala, Arg, Ser, Val or absent
<220> FEATURE:
<221> NAME/KEY: MOD_RES
<222> LOCATION: (20)..(20)
<223> OTHER INFORMATION: Lys, His, Gln, Arg, alpha-methyl-Glu or absent
<220> FEATURE:
<221> NAME/KEY: MOD_RES
<222> LOCATION: (21)..(21)
<223> OTHER INFORMATION: Asp, Glu, Leu or absent
<220> FEATURE:
<221> NAME/KEY: MOD_RES
<222> LOCATION: (23)..(23)
<223> OTHER INFORMATION: Ile, Val or absent
<220> FEATURE:
<221> NAME/KEY: MOD_RES
<222> LOCATION: (24)..(24)
<223> OTHER INFORMATION: Arg, Ala, Cys, Glu, Lys, Gln, alpha-methyl-Glu
      or absent
<220> FEATURE:
<221> NAME/KEY: MOD_RES
<222> LOCATION: (27)..(27)
<223> OTHER INFORMATION: Val, Ala, Lys, Met, Gln, Arg or absent
<220> FEATURE:
<221> NAME/KEY: MOD_RES
<222> LOCATION: (28)..(28)
<223> OTHER INFORMATION: Gln, Lys, Asn or absent
<220> FEATURE:
<221> NAME/KEY: MOD_RES
<222> LOCATION: (29)..(29)
<223> OTHER INFORMATION: Lys, Ala, Gly, Thr or absent

<400> SEQUENCE: 19

Xaa Xaa Gln Gly Thr Phe Thr Ser Asp Tyr Ser Lys Tyr Leu Xaa Xaa
1               5                   10                  15

Xaa Xaa Xaa Xaa Xaa Phe Xaa Xaa Trp Leu Xaa Xaa Xaa
            20                  25
```

GLUCAGON DERIVATIVES

CROSS-REFERENCE TO RELATED APPLICATIONS

This application is a divisional of U.S. application Ser. No. 15/539,238, filed Jun. 23, 2017, which is the National Stage of International Application No. PCT/KR2015/014481, filed Dec. 30, 2015, which claims priority from Korean Patent Application No. 10-2014-0193691, filed Dec. 30, 2014, the disclosures of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 14, 2019, is named 106132_000323_SL.txt and is 10 KB in size.

TECHNICAL FIELD

The present invention relates to a novel glucagon derivative having an excellent effect on both glucagon-like peptide-1 (GLP-1) receptors and glucagon receptors, and a composition for preventing or treating obesity containing the glucagon derivative as an active ingredient.

BACKGROUND ART

Recent economic advances and lifestyle changes have been accompanied by great changes in dietary habit. In particular, busy people of today are becoming overweight and obese due to high-calorie diets and insufficient exercise. According to a report of the World Health Organization (WHO), more than one billion adults are overweight worldwide, among them over three million are clinically diagnosed with severe obesity, and 250,000 people in Europe and 2.5 million people worldwide died of overweight- or obesity-related diseases every year (World Health Organization, Global Strategy on Diet, Physical Activity and Health, 2004).

Overweight and obesity increase blood pressure and blood cholesterol level, thus becoming a cause of various diseases including heart disease, diabetes, arthritis, etc., or aggravating the diseases. Further, overweight and obesity are some of the main causes that increase the risk of diseases such as arteriosclerosis, hypertension, hyperlipidemia, and heart disease in children and adolescents as well as in adults.

As such, obesity is now recognized as a serious disease prevalent all over the world and is a cause of various diseases. However, since obesity is believed to be overcome by self-help efforts, obesity patients are being evaluated as people with low self-control. Nevertheless, obesity is not readily curable because it is a complicated disease closely associated with appetite control and a mechanism of action for energy metabolism. Accordingly, for obesity treatment, it is required that both an individual effort for appetite control and treatment of an abnormal mechanism of action for energy metabolism be conducted concurrently. In this regard, there has been a need for the development of a drug capable of treating the abnormal mechanism of action.

As a result of the above effort, anti-obesity drugs such as Rimonabant® (Sanofi-Aventis), Sibutramin® (Abbott), Contrave® (Takeda), Orlistat® (Roche), etc., have been developed. However, these drugs had drawbacks such as fatal adverse reactions or little efficacy in treating obesity. For example, Rimonabant® shows an adverse reaction of central nervous system disorder, Sibutramin® and Contrave® show adverse cardiovascular effects, and Orlistat® shows an effect of body weight decrease of only about 4 kg after one year of administration. Accordingly, there appears to be no sure anti-obesity drug to be safely prescribed to obesity patients.

As such, active research has been conducted to develop a new pharmaceutical drug to resolve the problems in the conventional anti-obesity drugs, and recently, keen attention has been paid to glucagon derivatives. Glucagon is secreted by the pancreas when the blood glucose level falls low due to, for example, drug treatment, diseases, hormones, or enzyme deficiency. Glucagon signals the liver to break down glycogen to glucose and raise the blood glucose level to return to its normal level. Furthermore, glucagon has been reported to have an anti-obesity effect, in addition to the effect of raising the blood glucose level, by suppressing appetite and activating hormone-sensitive lipase in fat cells, thereby promoting fat decomposition.

Glucagon-like peptide-1 (hereinafter, referred to as 'GLP-1'), a glucagon derivative, is a substance under development as a drug to improve hyperglycemia in diabetic patients. GLP-1 has the functions of increasing insulin synthesis and promoting its secretion, inhibiting glucagon secretion, inhibiting gastric emptying, enhancing the use of glucose, and inhibiting food intake. Also, exendin-4, which is secreted by lizard venom and shows about 50% homology in amino acid sequence with GLP-1 is known to alleviate hyperglycemia in diabetes patients by activating the GLP-1 receptor. However, anti-obesity drugs containing GLP-1 or exendin-4 have been reported to have adverse effects of causing vomiting and nausea.

In this regard, as a GLP-1 alternative, oxyntomodulin, which can bind to both GLP-1 and glucagon peptides, has been highlighted. Oxyntomodulin is a peptide made from pre-glucagon, the precursor of glucagon, and has the same effects of GLP-1 such as inhibiting food intake, promoting satiety, and fat decomposition, thus raising its potential as an anti-obesity agent.

However, oxyntomodulin or its derivatives have a drawback in that they should be administered daily at a high dose due to their short in vivo half-lives and low efficacies.

DISCLOSURE OF INVENTION

Technical Problem

The present inventors, in an effort to improve obesity treatment effect while reducing the dose, have developed a glucagon derivative with a partial modification in its amino acid sequence, and confirmed that the glucagon derivative has an excellent effect acting on both glucagon receptors and GLP-1 receptors, thereby completing the present invention.

Solution to Problem

The present invention has been made keeping in mind the above problems occurring in the prior art, and an object of the present invention is to provide a novel peptide showing an excellent obesity treatment effect.

Another object of the present invention is to provide a composition for preventing or treating obesity containing the peptide.

Advantageous Effects of Invention

The novel peptide of the present invention can markedly activate both GLP-receptors and glucagon receptors compared to the native glucagon, exhibiting an excellent anti-obesity effect even with a small amount of administration, and thus it can be widely used as a safe and effective agent for treating obesity.

Best Mode for Carrying Out the Invention

In order to accomplish the above objects, in an aspect, the present invention provides a novel peptide having an amino acid sequence of the following Formula 1:

(Formula 1)
(SEQ ID NO: 19)
X1-X2-QGTFTSDYSKYL-X15-X16-X17-X18-X19-X20-X21-F-X23-X24-W-L-X27-X28-X29 wherein X1 is histidine, desamino-histidyl, N-dimethyl-histidyl, β-hydroxy imidazopropionyl, 4-imidazoacetyl, β-carboxy imidazopropionyl, or tyrosine;

X2 is α-methyl-glutamic acid, aminoisobutyric acid (Aib), D-alanine, glycine, Sar(N-methylglycine), serine, or D-serine;

X15 is cysteine, aspartic acid, or glutamic acid;

X16 is glutamic acid, aspartic acid, serine, α-methyl-glutamic acid, or absent;

X17 is cysteine, glutamine, glutamic acid, lysine, arginine, serine, or absent;

X18 is cysteine, alanine, arginine, valine, or absent;

X19 is alanine, arginine, serine, valine, or absent;

X20 is lysine, histidine, glutamine, arginine, α-methyl-glutamic acid, or absent;

X21 is aspartic acid, glutamic acid, leucine, or absent;

X23 is isoleucine, valine, or absent;

X24 is arginine, alanine, cysteine, glutamic acid, lysine, glutamine, α-methyl-glutamic acid, or absent;

X27 is valine, alanine, lysine, methionine, glutamine, arginine, or absent;

X28 is glutamine, lysine, asparagine, or absent; and

X29 is lysine, alanine, glycine, threonine, or absent;

with the proviso that the amino acid sequence identical to SEQ ID NO: 1 is excluded.

The peptide of the present invention may include peptides, peptide derivatives, and peptide mimics thereof, which can activate both GLP-1 receptors and glucagon receptors by modifying part of amino acid(s) via substitution.

As used herein, the term "native glucagon" refers to native human glucagon having the amino acid sequence of (SEQ ID NO: 1)
His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr.

The present invention provides the peptides defined above as derivatives of native glucagon, and in defining the peptides provided in the present invention, the peptides are intended to differ from native glucagon only at position(s) X in the sequences by alteration(s).

In the sequence of Formula 1 according to the present invention, amino acids may be considered to be consecutively numbered from the first amino acid to the 29$^{th}$ amino acid in the conventional direction from the N-terminus to the C-terminus. Accordingly, the description on "position" in the sequence of Formula 1 should be interpreted in the same manner as in the descriptions on positions of native human glucagon and other molecules.

As used herein, the term "peptide" refers to a compound in the form where two or more amino acids are linked by peptide bond(s). For the purposes of the present invention, the peptide may refer to one which exhibits an anti-obesity effect by activating both GLP-1 receptors and glucagon receptors.

Throughout the present invention, three-letter codes generally allowed for different amino acids, such as α-aminoisobutyric acid (Aib), Sar(N-methylglycine), and α-methyl-glutamic acid, are used along with the conventional one-letter or three-letter codes for naturally occurring amino acids.

Additionally, the amino acids described in the present invention are abbreviated as shown below according to IUPAC-IUB nomenclature.

| | |
|---|---|
| alanine (A) | arginine (R) |
| asparagine (N) | aspartic acid (D) |
| cysteine (C) | glutamic acid (E) |
| glutamine (Q) | glycine (G) |
| histidine (H) | isoleucine (I) |
| leucine (L) | lysine (K) |
| methionine (M) | phenylalanine (F) |
| proline (P) | serine (S) |
| threonine (T) | tryptophan (W) |
| tyrosine (Y) | valine (V) |

The peptide, which has the amino acid sequence of Formula 1 according to the present invention, may include any peptide that can activate both glucagon receptors and GLP-1 receptors, via introduction of substitution, addition, deletion, or modification after translation (e.g., methylation, acylation, ubiquitination, and intramolecular covalent bonds) in the amino acid sequence of glucagon described by SEQ ID NO: 1.

For the substitution or addition of amino acids, atypical or non-naturally occurring amino acids may be used, in addition to the 20 amino acids conventionally observed in human proteins. Commercial providers of the atypical amino acids include Sigma-Aldrich, ChemPep, Genzyme Pharmaceuticals, etc. The sequences for the peptides including these atypical amino acids and those for typical peptides may be synthesized or purchased from the commercial peptide manufacturing companies, e.g., American Peptide Company or Bachem (USA) or Anygen (Korea), etc.

For increasing the effect of the peptide of the present invention on glucagon receptors and GLP-1 receptors, in the amino acid sequence represented by SEQ ID NO: 1, the first amino acid, histidine, may be substituted with 4-imidazoacetyl by deleting the α-carbon of histidine, substituted with desamino-histidyl by deleting the N-terminal amine group, substituted with N-dimethyl-histidyl by modifying the N-terminal amine group with two methyl groups, substituted with β-hydroxy imidazopropionyl by substituting the N-terminal amine group with a hydroxyl group, substituted with β-carboxy imidazopropionyl by substituting the N-terminal amine group with a carboxyl group, or substituted with tyrosine.

Additionally, the domain which binds to a GLP-1 receptor may be substituted with an amino acid that can strengthen the hydrophobic bond and the ionic bond. Furthermore, a partial sequence of the glucagon sequence may be substituted with the amino acid sequence of GLP-1 or the amino sequence of exendin-4 to increase the activity of the GLP-1 receptor.

Additionally, a partial sequence of the glucagon sequence may be substituted with a sequence that can strengthen α-helix. Preferably, the amino acid(s) of the Formula 1 at positions 10, 14, 16, 20, 24, and 28 may be substituted with the amino acid(s) composed of Tyr(4-Me), Phe, Phe(4-Me), Phe(4-Cl), Phe(4-CN), Phe(4-NO$_2$), Phe(4-NH$_2$), Phg, Pal, Nal, Ala(2-thienyl), or Ala(benzothienyl), which are known to assist in α-helix formation, or derivatives thereof. The kind and number of the amino acids or derivative thereof to be added for this purpose are not limited.

Additionally, preferably, at least one amino acid in at least one amino acid pair at positions 10 and 14, 12 and 16, 16 and 20, 20 and 24, and 24 and 28 of the amino acid sequence of the Formula 1 may be substituted with glutamic acid or lysine, resulting in a pair of glutamic acid and lysine, which can form a ring, and the number of rings for insertion is also not limited.

In an exemplary embodiment, the amino acid sequence of glucagon may be substituted with a sequence having an ability to bind to GLP-1 receptors so that the peptide can exhibit an excellent effect on both GLP-1 receptors and glucagon receptors.

Preferably, the peptide of the present invention may be, in the amino acid sequence of the Formula 1, a peptide,
wherein X1 is histidine;
X2 is α-methyl-glutamic acid;
X15 is cysteine or aspartic acid;
X16 is serine, glutamic acid, or aspartic acid;
X17 is arginine, lysine, glutamic acid, or cysteine;
X18 is cysteine, valine, or arginine;
X19 is alanine or valine;
X20 is glutamine, lysine, or histidine;
X21 is aspartic acid, glutamic acid, or eucine;
X23 is isoleucine or valine;
X24 is arginine, glutamic acid, or glutamine;
X27 is valine, lysine, or methionine;
X28 is glutamine, lysine, or asparagine; and
X29 is lysine, glycine, or threonine;
with the proviso that the amino acid sequence identical to SEQ ID NO: 1 is excluded.

More preferably, the peptide of the present invention may be a peptide including an amino acid sequence selected from the group consisting of amino acid sequences of SEQ ID NOS: 2 to 14.

The peptide of the present invention may be prepared by a standard synthesis method, a recombinant expression system, or any method known in the art. Accordingly, the glucagon analogue according to the present invention may be synthesized by numerous methods including the following:
(a) synthesizing a peptide by a step-wise method via a solid-phase or liquid-phase method, or a fragment assembly, separating the final peptide followed by purification;
(b) expressing a nucleic acid construct encoding the peptide in a host cell, and recovering the expression product from the host cell culture;
(c) performing an expression of the peptide-encoding nucleic acid construct within a cell-free tube, and recovering the expression product; or
(d) a method of obtaining fragments of a peptide by a random combination of (a), (b), and (c), connecting the fragments, thereby recovering the corresponding peptide.

The present inventors confirmed via in vitro experiments that the peptide of the present invention has an excellent effect on GLP-1 receptors and glucagon receptors, compared to native glucagon (see Table 2). Additionally, via in vitro experiments it was confirmed that the peptide of the present invention has an excellent inhibitory effect against feed intake in an obese animal model, thus demonstrating that the peptide of the present invention can exhibit an excellent anti-obesity effect even when a small amount is administered.

Accordingly, the peptide of the present invention is a dual agonist capable of stimulating cAMP formation in both GLP-1 receptors and glucagon receptors, and is expected to have a more excellent effect of treating obesity, compared to the existing glucagon. In this regard, the peptide of the present invention can provide a more attractive selection for treating obesity and obesity-related diseases.

The peptide of the present invention, being a dual agonist, can combine the effect of GLP-1 in food intake and the effect of glucagon in lipid metabolism, and thereby synergistically act to accelerate the removal of lipid accumulation and continuous decrease of body weight. The synergistic effect as a dual agonist may help reduce cardiovascular risk factors, such as high cholesterol and LDL, which may be completely independent of the effect on body weight.

Accordingly, the peptide of the present invention may be used as a pharmaceutical drug for preventing weight increase, promoting weight decrease, reducing overweight, and treating not only obesity including morbid obesity (e.g., via regulation of appetite, eating, food intake, calorie intake, and/or energy consumption) but also obesity-related diseases, including obesity-related inflammation, obesity-related gallbladder disease, obesity-induced sleep apnea, but not limited thereto, and health conditions. Additionally, the peptide of the present invention may be used for the treatment of medical conditions that can be associated with obesity, such as metabolic syndrome, hypertension, arteriosclerosis-inducing dyslipidemia, atherosclerosis, arteriosclerosis, coronary artery heart disease, stroke, etc. However, regarding these symptoms, the effect of the peptide of the present invention may be entirely or partially mediated through the body weight-related effects or may be independent of them.

In order to improve the therapeutic effect of the glucagon derivative of the present invention, the glucagon derivative may be modified using a conventional technique in the art, such as a modification of polymers such as polyethylene glycol (PEG), glycan, etc., or a fusion with albumin, transferring, fatty acid, immunoglobulin, etc. For example, at least one amino acid side chain in the compound of the present invention may be conjugated to a polymer in vivo so as to increase the solubility and/or half-life and/or increase bioavailability. These modifications are known to reduce the clearance of therapeutic proteins and peptides.

Preferably, the polymer may be water-soluble (amphipathic or hydrophilic), non-toxic, and pharmaceutically inactive, and more preferably, may include PEG, a homopolymer or copolymer of PEG, a monomethyl-substituted polymer of PEG (mPEG), or a poly-amino acid such as poly-lysine, poly-aspartic acid, and poly-glutamic acid.

It is obvious to those skilled in the art that the thus-modified glucagon derivatives have a more excellent therapeutic effect than native glucagon. Accordingly, the variants of the glucagon derivatives are also included in the scope of the present invention.

In another aspect, the present invention provides a polynucleotide encoding the peptide.

As used herein, the term "homology", used regarding polynucleotides, refers to a sequence similarity with a wild type amino acid sequence and a wild type nucleotide sequence, and includes gene sequences sharing at least 75% with the polynucleotide sequence encoding the polypeptide, preferably at least 85%, more preferably at least 90%, and even more preferably at least 95%. These homology comparisons may be performed by the naked eye or using a comparison program which can be easily purchased. The computer programs available on the market can calculate the homologies between two or more sequences as a percentage. The homology (%) may be calculated on the neighboring sequences.

The peptide may be obtained in a large amount by inserting the peptide-encoding polynucleotide into a vector followed by its expression.

In this kind of recombinant expression, the polynucleotide of the present invention is generally inserted into an appropriate vector, and forms a cloning or recombinant vector possessing the polynucleotide, and the vector is also included in the scope of the present invention.

As used herein, the term "recombinant vector" refers to a DNA construct, which includes the nucleotide sequence of a polynucleotide encoding the target peptide which is operably linked to an appropriate regulatory sequence capable of expressing the target peptide in a suitable host cell. The regulatory sequence may include a promoter capable of initiating transcription, an operator sequence for regulating the transcription, a sequence encoding an appropriate mRNA ribosome-binding domain, and a sequence for regulating the termination of transcription and translation. The recombinant vector, once transformed into a suitable host cell, can replicate or function irrespective of the host genome, and may be integrated into the genome itself.

The recombinant vector to be used in the present invention is not particularly limited, as long as it is replicable in a host cell, and may be constructed using any vector known in the art. Examples of the conventional vectors to be used may include wild type or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used. As a plasmid vector, a pBR-based, a pUC-based, a pBluescriptII-based, a pGEM-based, a pTZ-based, pCL-based, and a pET-based plasmid may be used. The vectors to be used in the present invention are not particularly limited, but any vector known in the art may be used.

The recombinant vector may be used for the transformation of a host cell in order to produce the peptide of the present invention. Additionally, as part of the present invention, the transformed cell may be used for the amplification of nucleic acid fragments or replication of vectors of the present invention, or a cultured cell or cell line used for the recombinant production of the peptide of the present invention.

As used herein, the term "transformation" refers to introduction of a recombinant vector including a polynucleotide encoding the target protein into a host cell so that the target protein encoded by the polynucleotide can be expressed in the host cell. It does not matter whether the polynucleotide is inserted to be positioned within the chromosome or outside the chromosome, as long as the transformed polynucleotide can be expressed in the host cell.

Additionally, the polynucleotide includes DNA and RNA, which encode the target protein. The polynucleotide may be introduced in any form, as long as the polynucleotide can be expressed after being introduced into a host cell. For example, the polynucleotide may be introduced into a host cell in the form of an expression cassette, which is a genomic structure including all essential features required for self-expression. The expression cassette may generally include a promoter, which is operably linked to the polynucleotide, a transcription termination signal, a ribosome-binding domain, and a translation termination signal. The expression cassette may be a self-replicable expression vector. Additionally, the polynucleotide itself may be inserted into a host cell and operably linked to a sequence necessary for its expression in the host cell, but is not limited thereto.

Additionally, as used herein, the term "operably linked" refers to a state, in which a promoter sequence, which initiates and mediates transcription of the target protein-encoding polynucleotide, is functionally linked to the gene sequence.

The host cell suitable for the present invention is not particularly limited, as long as the host cell can express the polynucleotide of the present invention. Examples of the host cells to be used in the present invention may include *Escherichia* sp. such as *E. coli*; *Bacillus* sp. such as *Bacillus subtilis*; *Pseudomonas* sp. such as *Pseudomonas putida*; yeasts such as *Pichia pastoris, Saccharomyces cerevisiae*, and *Schizosaccharomyces pombe*; insect cells such as *Spodoptera frugiperda* (SF9); and animal cells such as CHO, COS, BSC, etc.

In another aspect, the present invention provides a pharmaceutical composition for preventing or treating obesity containing the peptide as an active ingredient.

As used herein, the term "prevention" refers to any action resulting in suppression or delay of the onset of obesity by the administration of the peptide or the pharmaceutical composition of the present invention, and the term "treatment" refers to any action resulting in improvement in symptoms of obesity or the beneficial alteration by the administration of the peptide or the pharmaceutical composition of the present invention.

As used herein, the term "administration" refers to introducing a particular substance to a patient in an appropriate manner. The administration route of the pharmaceutical composition of the present invention, although not particularly limited, may be any of the common routes, as long as the pharmaceutical composition can reach the target tissue in the body, e.g., intraperitoneally, intravenously, intramuscularly, subcutaneously, intradermally, orally, topically, intranasally, intrapulmonarily, intrarectally, etc.

As used herein, the term "obesity" refers to a medical condition in which excess body fat has accumulated in the body, and people are considered as obese when the body mass index (BMI; a measurement obtained by dividing a person's weight in kilograms divided by the square of height in meters) is 25 or higher. Obesity is generally induced by energy imbalance due to calorie intake being higher than energy consumption. Obesity is a metabolic disease, which can induce diabetes and hyperlipidemia, increase the risk of sexual dysfunction, arthritis, and cardiovascular disease, and in some cases, is also associated with the occurrence of cancer.

The pharmaceutical composition of the present invention may include a pharmaceutically acceptable carrier, excipient, or diluent.

As used herein, the term "pharmaceutically acceptable" refers to a sufficient amount, which can exhibit a therapeutic effect but does not incur any adverse reactions, and may be easily determined by those skilled in the art according to factors known in the medicinal field, such as the type of diseases to be treated, the patient's age, weight, gender, sensitivity to drugs, administration routes, number of administration, drug(s) to be combined or concurrently used, etc.

The pharmaceutical composition of the present invention may further include a pharmaceutically acceptable carrier. For oral administration, the pharmaceutically acceptable carrier may include, although is not limited to, a binder, a lubricant, a disintegrator, an excipient, a solubilizer, a dispersing agent, a stabilizer, a suspending agent, a coloring agent, and a perfume. For injectable administration, a buffering agent, a preserving agent, an analgesic, a solubilizer, an isotonic agent, and a stabilizer may be mixed for use. For topical administration, the pharmaceutically acceptable carrier may include a base, an excipient, a lubricant, a preserving agent, etc.

The pharmaceutical composition of the present invention may be formulated into various dosage forms in combination with the pharmaceutically acceptable carrier. For example, for oral administration, the pharmaceutical composition may be formulated into tablets, troches, capsules, elixirs, suspensions, syrups, wafers, etc. For injectable administration, the pharmaceutical composition may be formulated into an ampoule as a unit dosage form or a multi-dose administration. The pharmaceutical composition may be also formulated into solutions, suspensions, tablets, pills, capsules, and long-acting preparations.

On the other hand, examples of the carrier, excipient, and diluent suitable for the pharmaceutical composition of the present invention may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, mineral oils, etc. In addition, the pharmaceutical composition of the present invention may further include fillers, anti-coagulating agents, lubricants, humectants, perfumes, antiseptics, etc.

Additionally, the pharmaceutical composition may be formulated into one selected from the group consisting of tablets, pills, powders, granules, capsules, suspensions, liquid medicine for internal use, emulsions, syrups, sterile aqueous solutions, non-aqueous solvents, freeze-dried formulations, and suppositories.

Additionally, the pharmaceutical composition may be formulated into a suitable formulation for unit administration into a patient's body according to the conventional method, preferably into a formulation type useful for the administration of a peptide drug, and administered orally or parenterally via a subcutaneous, intravenous, intramuscular, intraarterial, intermedullary, intrathecal, intraventricular, intrapulmonary, intradermal, subcutaneous, intraperitoneal, intranasal, intragastric, local, sublingual, intravaginal, or intrarectal route according to the conventional method, but is not limited thereto.

Additionally, the peptide may be used by mixing with various carriers, such as a saline solution or an organic solvent, which are accepted as pharmaceutical drugs. For increasing stability or absorbency, the peptide may be used along with carbohydrates such as glucose, sucrose or dextran, or antioxidants such as glutathione, chelating agents, low molecular weight proteins, or other stabilizers, etc.

The amount and number of administration of the pharmaceutical composition of the present invention may be determined according to the types of drugs as active ingredients, along with other factors such as the diseases to be treated, administration routes, the patient's age, gender, weight, severity of the illness, etc.

The total effective dose of the composition of the present invention may be administered to a patient as a single dose, or as a multiple dose for a long-term period according to the fractionated treatment protocol. The pharmaceutical composition of the present invention may have a different content of the active ingredient according to the severity of the disease. Preferably, the total dose of the peptide of the present invention may be about 0.0001 µg to 500 mg per 1 kg of the patient's body weight. However, regarding the dose of the peptide, the effective dose is determined considering various factors such as the patient's age, weight, health conditions, gender, severity of illness, diet and excretion rate, etc., those skilled in the art can determine the appropriate effective dose according to the particular use of the composition of the present invention.

The formulations, administration routes, and administration methods of the pharmaceutical composition of the present invention may not be particularly limited, as long as the pharmaceutical composition can show the effect of the present invention.

Since the pharmaceutical composition of the present invention has an excellent in vivo duration and titer, the number and frequency of administration of the pharmaceutical composition of the present invention may be significantly reduced.

The pharmaceutical composition may be administered alone or in combination with other pharmaceutical formulations exhibiting an effect of preventing or treating obesity. The pharmaceutical formulation exhibiting an effect of preventing or treating obesity may include, although is not particularly limited to, a GLP-1 receptor agonist, a leptin receptor agonist, a DPP-IV inhibitor, a Y5 receptor antagonist, a melanin-concentrating hormone (MCH) receptor antagonist, a Y2/3 receptor agonist, an MC3/4 receptor agonist, a gastric/pancreatic lipase inhibitor, a 5HT2c agonist, a 3A receptor agonist, an amylin receptor agonist, a ghrelin antagonist, and/or a ghrelin receptor antagonist, etc.

In another aspect, the present invention provides a method for preventing or treating obesity including administering the peptide or a pharmaceutical composition containing the peptide to a subject.

As used herein, the term "subject" refers to a subject suspected of having obesity or being at risk for having obesity, and specifically, referring to mammals, including humans, rats, and cattle, but the subject may be any subject that can be treated by the peptide of the present invention, without limitation. The administration of a pharmaceutical composition containing the peptide of the present invention can effectively treat a subject suspected of having obesity, and the obesity is the same as described above.

The therapeutic method of the present invention may include administering a pharmaceutically effective amount of the pharmaceutical composition containing the peptide. The total daily dose of the composition can be determined through appropriate medical judgment by a physician, and the composition may be administered once or in a few divided doses. However, in view of the purpose of the present invention, the specific therapeutically effective dose of the composition for any particular patient may vary depending on various factors well known in the medical field, including the kind and degree of responses to be achieved, specific compositions according to whether or not other agents are used therewith, the patient's age, body weight, health conditions, gender and diet, time and route of administration, the discharge rate of the composition, the duration of treatment, other drugs used in combination or concurrently with the composition of the present invention, and other factors known in the medical field.

In still another aspect, the present invention provides a use of the peptide, in preparing a pharmaceutical drug for preventing or treating obesity.

Mode for the Invention

Hereinafter, the present invention will be described in more detail with reference to the following Examples. However, these Examples are for illustrative purposes only, and the invention is not intended to be limited by these Examples.

EXAMPLE 1

Production of Cell Lines for In Vivo Activation

<1-1 Production of Cell Lines Showing cAMP Response to GLP-1

A PCR reaction was performed using the open reading frame (ORF) of cDNA (OriGene Technologies, Inc., USA) of a human GLP-1 receptor gene as a template along with the forward and reverse primers represented by SEQ ID NOS: 15 and 16, which include the restriction sites for HindIII and EcoRI, respectively.

In particular, the PCR reaction was performed (denaturing at 95° C. for 60 seconds, annealing at 55° C. for 60 seconds, and elongation at 68° C. for 30 seconds) for 30 cycles. The PCR product was electrophoresed on a 1.0% agarose gel, and a 405 bp fragment was obtained therefrom via elution.

```
forward primer:
                                    (SEQ ID NO: 15)
5'-CCCGGCCCCCGCGGCCGCTATTCGAAATAC-3' reverse primer:
                                    (SEQ ID NO: 16)
5'-GAACGGTCCGGAGGACGTCGACTCTTAAGATAG-3'
```

The PCR product was cloned into a known animal cell expression vector, x0GC/dhfr (Korea Patent No. 10-0880509, the same herein after), to construct a recombinant vector, x0GC/GLPIR.

The thus-constructed recombinant vector, x0GC/GLPIR, was transformed into cells of the Chinese hamster ovary cell line CHO DG44, which were cultured in a DMEM/F12 medium containing 10% FBS, using Lipofectamine (Invitrogene, USA), and selected and cultured in a selective medium containing G418 (1 mg/mL) and methotraxate (10 nM). Monoclone cell lines were selected therefrom, and among them, the cell lines showing excellent cAMP responses to GLP-1 in a dose-dependent manner were finally selected.

<1-2> Production of Cell Lines Showing cAMP Response to Glucagon

A PCR reaction was performed using the open reading frame (ORF) of cDNA (OriGene Technologies, Inc., USA) of a human glucagon receptor gene as a template along with the forward and reverse primers represented by SEQ ID NOS: 17 and 18, which include the restriction sites for EcoRI and XhoI, respectively.

In particular, the PCR reaction was performed (denaturing at 95° C. for 60 seconds, annealing at 55° C. for 60 seconds, and elongation at 68° C. for 30 seconds) for 30 cycles. The PCR product was electrophoresed on a 1.0% agarose gel, and a 435 bp fragment was obtained therefrom via elution.

```
forward primer:
                                    (SEQ ID NO: 17)
5'-CAGCGACACCGACCGTCCCCCCGTACTTAAGGCC-3' reverse primer:
                                    (SEQ ID NO: 18)
5'-CTAACCGACTCTCGGGGAAGACTGAGCTCGCC-3'
```

The PCR product was cloned into the known animal cell expression vector, x0GC/dhfr, to construct a recombinant vector, x0GC/GCCR.

The thus-constructed recombinant vector, x0GC/GCCR, was transformed into cells of the Chinese hamster ovary cell line CHO DG44, which were cultured in a DMEM/F12 medium containing 10% FBS, using Lipofectamine (Invitrogene, USA), and selected and cultured in a selective medium containing G418 (1 mg/mL) and methotraxate (10 nM). Monoclone cell lines were selected therefrom, and among them, the cell lines showing excellent cAMP responses to glucagon in a dose-dependent manner were finally selected.

EXAMPLE 2

Synthesis of Glucagon Derivatives

In order to develop a glucagon derivative having an excellent effect on both GLP-1 receptors and glucagon receptors, the amino acid sequence of native glucagon represented by SEQ ID NO: 1 was substituted with an amino acid sequence which has an ability to bind to GLP-1 receptors, and glucagon derivatives were synthesized as shown in Table 1 below.

TABLE 1

| SEQ ID NO | Amino Acid Sequence |
| --- | --- |
| SEQ ID NO: 1 | HSQGTFTSDYSKYLDSRRAQDFVQWLMNT |
| SEQ ID NO: 2 | HXQGTFTSDYSKYLDEKCAKEFIQWLVNT |
| SEQ ID NO: 3 | HXQGTFTSDYSKYLDEKCVKLFIQWLVNT |
| SEQ ID NO: 4 | HXQGTFTSDYSKYLDEKCAKEFVEWLVNT |
| SEQ ID NO: 5 | HXQGTFTSDYSKYLDEKCAHEFVEWLVNT |
| SEQ ID NO: 6 | HXQGTFTSDYSKYLDSKCAHEFVEWLVNT |
| SEQ ID NO: 7 | HXQGTFTSDYSKYLDSKCVHEFIEWLKNT |
| SEQ ID NO: 8 | HXQGTFTSDYSKYLDSKCAHEFIEWLKNK |
| SEQ ID NO: 9 | HXQGTFTSDYSKYLDSECAHEFIEWLKQG |
| SEQ ID NO: 10 | HXQGTFTSDYSKYLDDKCAHEFVEWLVNT |
| SEQ ID NO: 11 | HXQGTFTSDYSKYLDEECAKEFIRWLKKG |
| SEQ ID NO: 12 | HXQGTFTSDYSKYLCEKRAKEFVQWLMNT |
| SEQ ID NO: 13 | HXQGTFTSDYSKYLDECRAKEFVQWLMNT |
| SEQ ID NO: 14 | HXQGTFTSDYSKYLDEKCAKEFVQWLMNT |

In Table 1 above, the amino acid indicated as "X" in the sequences of SEQ ID NOS: 2 to 14 represents α-methyl-glutamic acid, which is a non-native amino acid, and the lysine residue in these sequences can form a ring with glutamic acid residue.

EXAMPLE 3

Measurement of In Vitro Activity of Glucagon Derivatives

In order to measure the anti-obesity activities of the glucagon derivatives synthesized in Example 2, the in vitro cellular activities of the glucagon derivatives were measured using the transformed cell lines prepared in Examples 1-1 and 1-2.

The transformed cell lines were prepared so that the human GLP-1 receptor gene and the human glucagon receptor gene can be expressed in CHO, respectively, and are suitable for measuring the activities of GLP-1 and glucagon. Accordingly, the activities of glucagon derivatives synthesized according to the present invention were measured using the transformed cell lines, respectively.

Specifically, the transformed cell lines were subcultured two or three times per each week, aliquoted into a 96-well plate with 1×10$^5$ cells/well, and cultured for 24 hours, respectively.

The cultured cells were washed with Krebs-Ringer Bicarbonate (KRB) buffer solution, suspended in 40 mL of KRB buffer solution containing 1 mM 3-isobutyl-1-methylxanthine (IBMX), and placed at room temperature for 5 minutes.

The native glucagon (SEQ ID NO: 1) or glucagon derivatives (representatively, peptides of SEQ ID NOS: 12 to 14) according to the present invention were subjected to serial dilution at 5-fold intervals ranging from 1000 nM to 0.02 nM, 40 mL of the above cells were added thereto, and cultured in a $CO_2$ incubator at 37° C. for 1 hour.

Then, 20 mL of cell lysis buffer was added to the respective resultants, and the cell lysates were applied to a cAMP assay kit (Molecular Device, USA) to measure cAMP concentration, and $EC_{50}$ values were calculated and compared therebetween. The results are shown in Table 2 below.

TABLE 2

| Test Material | $EC_{50}$ (nM) | |
| --- | --- | --- |
| | hGLP-IR | hGCGR |
| GLP-1 | 0.36 | >1,000 |
| glucagon | >1,000 | 1.48 |
| SEQ ID NO: 12 | 0.96 | 1.38 |
| SEQ ID NO: 13 | 0.27 | 0.23 |
| SEQ ID NO: 14 | 0.17 | 0.38 |

As shown in Table 2 above, the glucagon derivatives according to the present invention showed excellent effects on both GLP-1 receptors and glucagon receptors, compared to the native glucagon represented by SEQ ID NO: 1.

Glucagon is known to have an obesity treatment effect by activating GLP-1 receptors and glucagon receptors, thereby suppressing appetite, improving satiety, and promoting fat cell lysis. Since the glucagon derivatives according to the present invention are now shown to have excellent in vitro effects on both GLP-1 receptors and glucagon receptors, compared to the native glucagon, these glucagon derivatives can be used as a more effective agent for treating obesity than the existing glucagon.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A peptide comprising the amino acid sequence of SEQ ID NO: 13.

2. The peptide of claim 1, wherein the peptide is capable of activating a GLP-1 receptor and a glucagon receptor.

3. The peptide of claim 1, wherein the peptide has an anti-obesity effect.

4. The peptide of claim 1, wherein at least one amino acid pair at positions 12 and 16 or 16 and 20 of the peptide forms a ring.

5. A pharmaceutical composition comprising the peptide of claim 1 as an active ingredient.

6. The pharmaceutical composition of claim 5, further comprising a pharmaceutically acceptable carrier.

7. The pharmaceutical composition of claim 5, wherein the pharmaceutical composition is administered alone or in combination with other pharmaceutical formulations exhibiting an effect of treating obesity.

8. The pharmaceutical composition of claim 7, wherein the other pharmaceutical formulations exhibiting an effect of treating obesity are a GLP-1 receptor agonist, a leptin receptor agonist, a DPP-IV inhibitor, a Y5 receptor antagonist, a melanin-concentrating hormone (MCH) receptor antagonist, a Y2/3 receptor agonist, an MC3/4 receptor agonist, a gastric/pancreatic lipase inhibitor, a 5HT2c agonist, a 3A receptor agonist, an amylin receptor agonist, a ghrelin antagonist, or a ghrelin receptor antagonist.

9. A method for treating obesity, comprising administering the pharmaceutical composition of claim 5 to a subject in need thereof.

10. A method for treating obesity, comprising administering the peptide of claim 1 to a subject in need thereof.

* * * * *